United States Patent [19]

Myers et al.

[11] Patent Number: 5,087,616

[45] Date of Patent: Feb. 11, 1992

[54] CYTOTOXIC DRUG CONJUGATES AND THEIR DELIVERY TO TUMOR CELLS

[75] Inventors: Andre E. Myers, Genevea, Switzerland; Daniel Bichon, Thorens-Glieres, France

[73] Assignee: Battelle Memorial Institute, Geneva, Switzerland

[21] Appl. No.: 82,244

[22] Filed: Aug. 6, 1987

[30] Foreign Application Priority Data

Aug. 7, 1986 [EP] European Pat. Off. ............ 86810347

[51] Int. Cl.$^5$ .................... A61K 37/36; A61K 37/02; C07K 13/00

[52] U.S. Cl. ........................................ 514/21; 514/12; 530/345; 530/399; 530/342; 530/408; 530/409; 530/410

[58] Field of Search ................ 530/345, 399, 408–410, 530/389–391; 514/21, 12

[56] References Cited

U.S. PATENT DOCUMENTS

| | | | |
|---|---|---|---|
| 3,917,824 | 11/1975 | Camble et al. | 514/2 |
| 4,485,093 | 11/1984 | Runge | 412/85 |
| 4,528,186 | 7/1985 | Nishimura et al. | 514/2 |
| 4,545,985 | 10/1985 | Pastan et al. | 514/2 |

FOREIGN PATENT DOCUMENTS

| | | |
|---|---|---|
| 0046039 | 7/1981 | European Pat. Off. . |
| 0112720 | 12/1983 | European Pat. Off. . |
| 0128733 | 6/1984 | European Pat. Off. . |
| 0131868 | 7/1984 | European Pat. Off. . |
| 0259904A | 3/1988 | European Pat. Off. . |
| WO8304030 | 11/1983 | PCT Int'l Appl. . |
| WO8500369 | 1/1985 | PCT Int'l Appl. . |
| WO8501284 | 3/1985 | PCT Int'l Appl. . |

OTHER PUBLICATIONS

Thorpe, Philip, Ph.D., Tumor Imaging and Drug Targeting, British Med. Bul. (1984), vol. 40, No. 3, pp. 233-239.

Hurwitz et al., The Covalent Binding of Daunomycin and Adriamycin to Antibodies, with Retention of Both Drug and Antibody Activities; Cancer Res. 35, 1175-1181, May 1975.

Kato et al., Antitumor Activity of 1—D-Arabinofuranosylcytosine Conjugated with Polyglutamic Acid and Its Derivative, Cancer Res. 44, 25-30, 1984.

Masquelier et al., Amino Acid and Dipeptide Derivatives of Daunorubicin, J. Med. Chem, 1980, 23, 1166-1177.

O'Keefe et al., Characterization of a Transferrin-Diphtheria Toxin Conjugate, The Journal of Biological Chem., 1985, vol. 260, No. 2, 932-937.

Bacha et al., Thyrotropin-Releasing Hormone-Diphtheria Toxin-Related Polypeptide Conjugates, The Journal of Biological Chem., vol. 258, No. 3, 1565-1570, 1983.

Murphy et al., Genetic Construction, Expression, and Melanoma-Selective Cytotoxicity of a Diphtheria Toxin-Related α-Melanocyte-Stimulating Hormone Fusion Protein, Proc. Natl. Acad. Sci., vol. 83, 8258-8262, 1986.

(List continue on next page.)

*Primary Examiner*—F. T. Moezie
*Attorney, Agent, or Firm*—Cushman, Darby & Cushman

[57] ABSTRACT

A therapeutic composition comprising a chemical conjugatge including a first moiety, other than an immunoglobulin or fragment thereof, such as epidermal growth factor, which preferentially binds to a tumor cell, and is internalized by the cell, and a second moiety linked to the first moiety, and comprising a biodegradable polymeric carrier, such as polyglutamic acid, to which one or more cytotoxic molecules, for instance, daunomycin, are attached. The degradation of the carrier by intracellular enzymes releases a cytotoxic agent, resulting in selective destruction of the tumor cells.

10 Claims, 2 Drawing Sheets

OTHER PUBLICATIONS

Pastan et al., Immunotoxins, Cell, vol. 47, 641-648, 186;
Potman et al., Optimization of Macromolecular Prodrugs of the Antitumor Antibiotic Adriamycin, Journal of Controlled Re. 2, (1985), 205-213.
Kato et al., A Novel Method of Conjugation of Daunomycin with Antibody with a Poly-L-Glutamic Acid Derivative as Intermediate Drug Carrier, J. Med. Chem., 1984, 27, 1602-1607.
Shimiazu et al., A Cytotoxic Epidermal Growth Factor Cross-Linked to Diphtheria Toxin A-Fragment, vol. 118, No. 2, 1980.
Cawley et al., Epidermal Growth Factor-Toxin A Chain Conjugates: EGF-Ricin A is a Potent Toxin While EGF-Diphtheria Fragment A is Nontoxic, Cell, vol. 22, 563-570, 1980.
Simpson et al., Killing of Cultured Hepatocytes by Conjugates of Asialofetuin and EGF Linked to the A Chains Ricin or Diphtheria Toxin, Cell, vol. m29, 469-473, 1982.

CYTOTOXIC DRUG CONJUGATES AND THEIR DELIVERY TO TUMOR CELLS

BACKGROUND OF THE INVENTION

1. Field of the Invention

The present invention deals with novel chemical conjugates for the selective delivery of cytotoxic drugs to tumor cells, and with methods of destroying tumor cells using such conjugates.

2. Background of the Invention

It is well known that current cancer therapy involves the use of antimitotic drugs such as adriamycin, vincristine, cisplatin, daunomycin and methotrexate, which all have strong undesirable side-effects on the normal cells of the patient. It is therefore important that the activity of antitumor drugs be specifically directed to the malignant cells and have little toxic effect on the normal cells.

One approach to selectively delivering cytotoxic agents to tumor cells requires use of antibodies which preferentially bind tumor-associated or tumor-specific antigens such as alpha fetoprotein. The antibody may be radiolabeled, or it may be conjugated to toxins such as hematoporphyrin, abrin, ricin, diphtheria toxin, Pseudomonas exotoxin, gelonin or to the above-mentioned antimitotic drugs. For reviews see K. Sikora et al., (1984), Br. Med. Bull., 40, 233-9; and P. C. Thorpe, et al., (1985), in Monoclonal Antibodies B4, Biological & Clinical Applications. Further, Pastan, U.S. Pat. No. 4,545,985 discloses the binding of Pseudomonas exotoxin to antibodies, for instance antibodies to specific human cell receptors such as the transferrin receptor.

There are a number of disadvantages in the use of antibodies as targeting agents, as described by I. Pastan, et al., (1986), Cell, 47, 641-648. First, the internalization of antibody conjugates into cells is highly variable, depending on the antibody and the cell. Second, the antibody may itself be antigenic and stimulate an immune response in the patient, which would limit the effectiveness of the conjugate. Third, the antibody may bind to normal cells, which do not have the antigen recognized by the antibody, by means of Fc receptors that occur on many nontumor cells and can react with many antibodies. Fourth, it is difficult to attach a large number of drug molecules to an antibody without adversely affecting its antigen-binding activity [Hurwitz, et al., (1975), Cancer Res., 35, 1175-1181]. Finally, the high molecular weight of antibodies reduces their ability to penetrate into tumors between the cells [See Delabye, et al., (1986), J. Clin. Invest. 77: 301-11; Buchegger, et al. (1983), J. Exp. Med 158: 413-27; Buchegger et al. (1986), Cancer,58, 655-61.]

Another approach is to attach the drug to a polyaminoacid carrier which reduces its cytotoxic action in normal cells. This carrier may bear a large number of drug molecules. In the drug-carrier complex, the amino acid composition or sequence is intended to provide preferential release of the cytotoxin at tumor cells by means of degradative enzymes known to be present in elevated concentrations in tumor cells. For example, Zunino, et al., (1982), Int. J. Cancer 30, 465-70, reports on the antitumor activity of daunorubicin linked to poly-L-aspartic acid, and Kato, et al., (1984), Cancer Res. 44, 25, describes antitumor activity of cytosine arabinoside conjugated with polyglutamic acid. W.A.R. van Heeswijk, et al., (1985), J. Controlled Release 1, 301-315, and Hoes et al., (1985), J. Controlled Release 2, 205-213, describe additional conjugates of poly-glutamic acid backbones with peptide spacers to which adriamycin is covalently coupled.

The combination of a tumor-directed antibody and a degradable polyaminoacid carrier with a cytotoxic drug has also been described. For example, Kato, et al., (1984), J. Medicinal Chem. 27, 1602-1607, reports conjugation of daunomycin (DM) to polyglutamic acid (PGA) and coupling the resulting cytotoxic polymer with rat alpha fetoprotein (AFP) antibody. Upon trial, the cytotoxic activity of the resulting anti-AFP-PGA-DM conjugate was shown to be more effective than nIg (a control antibody), anti-AFP, unconjugated DM, PGA-DM or nIg-PGA-DM.

Similarly, EP-A 112,720 (Teijin) discloses a conjugate comprising an immunoglobulin capable of binding selectively to a particular antigen possessed by a cell to be killed, a polymer carrier and a cytotoxic substance linked thereto, for instance p-(N,N-bis(2-Chloroethyl))-phenylenediamine, melphalan, 1-(beta-D-arabinofuranosyl) cytosine and its phosphate, methotrexate, actinomycin D, mitomycin C and the like, while Runge, U.S. Pat. No. 4,485,093 discloses an immunotoxin conjugate for treating malignant diseases, which consists of arsanilic acid and tumor specific antibody covalently bound to a polyglutamic acid back-bone.

Unfortunately, the use of a polyaminoacid carrier does not solve all of the problems associated with the use of immunotoxins. In addition to the problems related to using antibodies directly conjugated to cytotoxins, addition of such carriers to antibodies, or even smaller Fab fragments, may undesirably further reduce their ability to penetrate tumors efficiently.

Pastan, U.S. Pat. No. 4,545,985 suggested conjugating Pseudomonas exotoxin (PE) to a variety of peptides, proteins and growth factors that react with specific receptors on cells, including sarcoma growth factors, melanocyte stimulating hormone, somatostatin, glucagon, insulin, transferrin, low density lipoprotein (LDL), calcitonin, alpha-2-macroglobulin and lysine bradykinin. Pastan constructed a conjugate of Pseudomonas exotoxin (PE) and a peptide hormone isolated from mice, Epidermal Growth Factor (EGF), by introducing thiol groups into each and then linking the two using a disulfide exchange reaction. The conjugate was toxic to KB tumor cells, but nude mice injected with the conjugate died of liver failure. The coupling destroyed the toxin's ability to bind to its own receptor, so toxicity was mediated by the EGF receptors of the liver cells.

N. Shimizu, et al., (1980), FEBS Letters 118, 274-278, reported the preparation of a covalent conjugate of EGF and diphtheria toxin. In addition, Cawley and Herschman, (1980), Cell 22, 563-570, and Simpson, et al., (1982), Cell 29, 469-673, reported on conjugates of EGF covalently linked to the polypeptide A chain of ricin, or to diphtheria toxin, by a disulfide bridge. These conjugates containing EGF generally showed high but unpredictably variable toxicity for various normal cells.

[For techniques of preparing or isolating EGF from various species, including the human form (also called urogastrone), or other variants or analogues thereof, and for discussion of their properties, see WO85/00369 (Chiron); WO83/04030 (Applied Molecular Genetics); Nishimura, U.S. Pat. No. 4,528,186; EP-A 46,039 (G.D. Searle); EP-A 128,733 (Genentech); Komoriya, WO85/01284; Wakanuga, EP-A 131,868; and Camble, U.S. Pat. No. 3,917,824.]

More recently, additional similar conjugates of non-immunoglobulin peptides and cytotoxins have been reported. For example, Bacha, et al., (1983), J. Biol. Chem. 258, 1565-1570, describes conjugates of thyrotropin-releasing hormone (TRH) and polypeptides related to diphtheria toxin, which were toxic to pituitary tumor cells; and O'Keefe and Draper, (1985), J. Biol. Chem., 260, 932-937, report on characterization of a transferrin-diphtheria toxin conjugate, which was toxic to mouse cell cultures. Furthermore, Murphy, et al., (1986), Proc. Nat. Acad. Sci., USA, 83, 8258-8262, describes melanoma-selective cytotoxicity of a genetically fused protein which is equivalent to a covalent conjugate of the alpha melanocyte-stimulating hormone (MSH) and a cytotoxin related to diphtheria toxin. JP 60163824 (Nippon Shinyaku KK) discloses a drug carrier, wherein the carrier comprises a protein, such as an apolipo-protein obtained from a serum lipoprotein (e.g., LDL), and a lipid, designed for selectively carrying the pharmaceutical ingredient to the necessary tissue.

Again, the number of toxin molecules that may be directly attached, as taught above, to a molecule of a peptide hormone or growth factor is limited by the need to preserve receptor binding activity. Furthermore, such conjugates of a non-immunoglobulin and a cytotoxin may be excessively toxic for normal cells bearing the appropriate receptors.

No admission is made that any of the foregoing references constitute "prior art" and all descriptions are based on the publications rather than on firsthand knowledge of the work described.

SUMMARY OF THE INVENTION

The invention resides in destroying tumor cells with a composition including a novel drug conjugate comprising:
  (a) A first moiety, "a homing agent", a non-immunoglobulin which preferentially binds to a tumor cell receptor, and
  (b) A second moiety, covalently linked to the first moiety, and comprising a biodegradable polymeric carrier to which one or more cytotoxic molecules are attached,
and where said conjugate is internalized by the cell. The degradation of the carrier by intracellular enzymes releases a cytotoxic agent, resulting in destruction of the cell. Preferably, the first moiety, besides specifically binding to the tumor cell, also promotes the internalization of the conjugate by that cell. It is also desirable that the carrier be particularly susceptible to tumor cell-associated intracellular enzymes in order to increase the therapeutic index of the conjugate.

The homing agent is preferably a peptide or protein growth factor. One particularly preferred class of homing agent includes mouse Epidermal Growth Factor, and other related growth factors, such as human EGF (urogastrone), alpha transforming growth factor (TGF alpha), and vaccinia virus growth factor, which bind preferentially to tumor cells bearing EGF-binding receptors and are efficiently internalized by those receptors. The growth factor may be purified from natural sources, synthesized by stepwise peptide synthesis or isolated from cells genetically engineered to express the factor. The agent may be a naturally occurring factor, a synthetic duplicate of that factor, or an active analogue or fragment of the factor. It may also be a substance which is a "pro" form of the factor, which the subject's body converts into the active form of the factor.

It should be noted that the spectrum of tumor cells to which these homing agents bind will differ from agent to agent. Human EGF (urogastrone), TGF alpha and vaccinia virus growth factor all bind to the same receptor (herein called the EGF receptor), with the same affinity, as does mouse EGF [DeLarco and Todaro (1978), Proc. Natl. Acad. Sci USA 75, 4001-4005], and therefore are expected to exhibit the same tumor specific binding as mouse EGF. Furthermore, as the names imply, EGF and related growth factors generally stimulate replication of cells when they bind to the EGF receptor. In addition, TGF alpha is produced by many solid human tumors [Derynck et al., (1987), Cancer Res. 47, 707-712)]in which it is thought to act as a self-stimulating (autocrine) growth factor [Sporn and Todaro, (1980), N. Engl. J. Med. 303, 878-880]. Delivery of a cytotoxic agent linked to TGF alpha (or any other EGF-related peptide) should be selectively toxic to these tumors, not only because of the receptor-mediated uptake of the agent, but also because the mitogenic action of the growth factor should induce increased susceptibility to antimitotic drugs and other toxins. In other words, since actively replicating cells are more vulnerable to the toxic actions of a variety of drugs, the homing agent can render cells which carry receptors more sensitive to drug killing action after the conjugate has entered the cells.

In particular, several investigators have demonstrated the presence of EGF receptors in high concentrations on many squamous cell carcinomas, as well as on other carcinomas, and also on sarcomas. Such results include breast, lung, brain and skin tumors. [See the following references: Liberman et al., (1984), Cancer Res 44, 753-760; Merlino et al., (1984), Science 224, 417-419; Kamata et al., (1986), Cancer Res. 46, 1648-1653; Singletary et al., (1987), Cancer Res 47, 403-406; Hunts et al., (1985), Jpn. J. Cancer Res. 76. 663-660; Barknecht et al., (1985), Other peptide factors, which are unrelated to EGF, may also serve in this invention as homing agents for different tumor cells. For instance, Platelet-Derived Growth Factor (PDGF) is a dimer composed of two related peptides, each with a MW of about 30,000 D, which is released from platelet granules when blood clots form. It is required by smooth muscle cells, fibroblasts and other mesenchymal cells, but not by epithelioid or hematopoietic cells [Cochran and Stiles, (1983), Cell 33, 939-347]. After binding to receptors on a cell, PDGF is internalized [Nilsson et al., (1983), Proc. Natl. Acad. Sci 80, 5592-5596]. A fusion protein containing 80 amino acids of the SV40 t antigen fused to the amino terminus of one chain of PDGF was active in internalization [Wang and Williams, (1984), J. Bio. Chem., 10645-10648], indicating that PDGF, like EGF, could be expected to carry material preferentially into cells bearing appropriate receptors.

PDGF is also known to be produced by some tumor cells in culture, including glioma, osteosarcoma, embryonal carcinoma, and a variety of neoplastically transformed fibroblasts [Van Zoelen et al., (1985), Mol. Cell. Biol. 5, 2289-2297], which suggests a possible self-stimulatory role like that postulated for TGF alpha. Thus PDGF may be useful for homing and internalization of cytotoxic conjugates of the invention into these tumors.

Another possible homing agent Nerve Growth Factor (NGF), which is a peptide of about the same MW as EGF, has little or no effect on differentiated glial cells, but significantly retards growth of undifferentiated glioma cells [Vinores and Koestner, (1980). Cancer Lett 10, 309-318]. NGF has been observed to decrease the specific induction of neural tumors by ethylnitrosourea [Vinores and Perez-Polo, (1980), J. Cancer Res. Clin. Oncol., 98. 59-63] and to reverse morphologic transformation of anaplastic gliomas [Koestner, (1985), Toxicol. Pathol. 13, 90-104]. Thus it appears that some brain tumors have the ability to recognize and respond to NGF.

Because normal differentiated glial cells are refractory to NGF, cytotoxic agents conjugated to NGF would be expected to preferentially destroy brain tumor cells which respond to NGF. Antibody to NGF has been used to diagnose and treat melanoma (Ross et al., EP 202,005; U.S. Pat. No. 723,760), which suggests that these tumors may also respond to NGF.

Transferrin could also be used as a homing agent to deliver cytotoxic drugs to tumors because, like EGF, transferrin-receptor complexes are internalized [Karin and Mintz (1981) J. Biol. Chem 256: 324-3252]. O'Keefe and Draper, (1985), J. Biol. Chem., 260, 932-937, reported that toxicity of a transferrin-diphtheria toxin conjugate was abolished in presence of excess transferrin, which indicates that this conjugate internalized via transferrin receptors. As disclosed by Pastan (U.S. Pat. No. 4,545,985), antibodies to the transferrin receptor can be used to deliver toxins to tumors, particularly adult T cell leukemia. Transferrin is also used in radioimaging of tumors [NTIS Tech Note, (1985), NTN85-0891], which indicates preferential binding of transferrin to these tumors. Additional peptide factors may also serve as the homing agent in the invention. For example, alpha melanocyte-stimulating hormone (alpha MSH), another small peptide hormone, was genetically fused to a cytotoxic protein, and the fusion protein reportedly was cytotoxic for melanoma cells [Murphy, et al., (1986), Proc. Nat. Acad. Sci., USA, 83, 8258-8262]. Also, thyrotropin-releasing hormone (TRH), a tripeptide, has been conjugated with polypeptides related to diphtheria toxin, and the resulting conjugates appeared to be internalized only by cells bearing TRH In selecting a homing agent, the following desiderata should be considered:
a) the homing substance must be highly specific for tumor cells, as opposed to normal cells;
b) the homing substance should bind to a receptor found in a wide range of tumor cells;
c) the homing substance should promote the internalization (receptor interaction) of the conjugates;
d) the homing substance should stimulate cell proliferation, therefore rendering the targeted cell more vulnerable to antimitotic action of the cytotoxin;
e) the homing substance should be sufficiently small to penetrate solid tumors efficiently;
f) suitable chemistry must exist for coupling the cytotoxic compound carrier to the homing agent.

The second moiety in the conjugate of the invention is a polymeric carrier for the cytotoxic agent and comprises a plurality of repeating units, each unit having the structure shown in formula (I) below:

wherein p is in the range of 0 to 20, preferably 1 or 2, where x is preferably in the range of 0-20, where A is a linker, preferably an amino acid, and where, if x is greater than 1, the amino acids $A_x$ may be the same or different. T is either hydroxyl or a cytotoxic substance. The units may be identical, or they may vary in p, x, $A_x$, or T. Of course, for the conjugate to have a cytotoxic effect, at least one of the units must bear a cytotoxic molecule.

Preferably, p is selected such that known amino acids can be utilized for synthesis of the polymeric second moiety. Thus, when p=1, the second moiety will be a polymer of a derivative of aspartic acid, and when p=2, a polymeric derivative of glutamic acid. Since p may be the same or different for each unit of the second moiety, when p=1 or 2 in the same polymer, the second moiety will be a copolymer of derivatives of aspartic and glutamic acids. The value of p may be lower than 1 or higher than 2, provided the biodegradability of the second moiety is maintained. In particular, greater values of p may be useful for presenting certain cytotoxic agents at a distance from the polymer backbone to facilitate access by enzymes which release the agent from the carrier.

More generally, each unit of the second moiety may have the following formula IA:

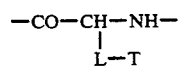

where L is a biodegradable linker and T is as defined in formula I.

The conjugate per se is preferably of reduced cytotoxicity to normal cells as compared to the substance T in its free form. Intracellular release of T in cytotoxic form is accomplished by cellular enzymes, preferably enzymes preferentially expressed in tumor cells.

The introduction of the side-chain extension $A_x$, where A may vary among the common amino-acids, and x is preferably in the range 0-20, involves the usual techniques of peptide synthesis. It is assumed that the preferential manifestation in malignant cells of the cytotoxicity typical of the free cytotoxic substance is a function of intracellular enzymatic degradation of the conjugate, liberating either the cytotoxic substance or active derivatives thereof. Preferential release within malignant cells may thus be governed by a differential in terms of type or enhanced level of enzymatic activity between malignant and normal cells.

An elevated level of proteolytic activity, including γ-glutamyl transferase activity is associated with a variety of tumors [see W.A.R. van Heeswijk, et al., (1984), in Recent Advances in Drug Delivery Systems, Proc. Int. Symp., 1983, Plenum Press, N.Y., Anderson, J. M. and Kim, S. W., eds., pp 77-100], possibly allowing for tumor specific release of the cytotoxic drug from secondary amide linkage directly with the γ-carboxyl of either the glutamic acid side chain of polyglutamic acid or from such linkage with a glutamyl residue within, or terminal in, Ax. In addition, such enzymatic cleavage at the polyglutamic acid γ-carboxyl, or general proteolytic cleavage within $A_x$ or of the polyglutamic acid polymer backbone, may release a peptidyl prodrug of the cytotoxic substance subject to further processing by lysosomal enzymes, and involving the γglutamyl transferase when the drug is γ-linked to glutamic acid in $A_x$.

The extent and rate of endocellular drug release may thus be significantly affected by variation in the length and nature of the $A_x$ moiety. Such processing by lysosomal enzymes of bovine serum albumin-daunomycin conjugate has been shown by A. Trouet, et al. [(1982), Proc. Natl. Acad. Sci., 79, 626: and (1980), J. Med. Chem., 23, 1166-1171] to vary widely with the length and sequence of the peptide moiety interspersed between the protein and the drug.

The cytotoxic substance is selected from agents inhibitory of DNA synthesis and function (e.g., adriamycin, daunomycin, bleomycin, melphalan, chlorambucil, cisplatin), of microtubule (mitotic spindle) formation and function (e.g., vinblastine, vincristine), or antimetabolites (e.g., methotrexate), or cytotoxic substances of these or other mechanisms of action. For compilations of antineoplastic drugs, see: A Synopsis of Cancer chemotherapy, R. T. Silver, R. D. Lauper and C. I. Jarowski, Dunn-Donnalley Publishing Corp., N.Y., 1977; Cancer Treatment Symposia: Compilation of Phase II Results with Single Antineoplastic Agents, NIH Publication No. 85-2739, 1985; NCI Investigational Drugs: Pharmaceutical Data, NIH Publication No. 86-2141, 1986.

Preferably at least 10 percent of the units of formula (I) bear a cytotoxic agent (not necessarily the same one for all units). However, higher levels of substitution are preferred unless they significantly reduce the cytospecificity of the conjugate.

The number of repeating units is not fixed, but is preferably in the range of 20-300. The MW of the polymeric carrier is preferably high enough so that, even if it becomes detached from the homing substance before entering tumor cells, it does not freely enter cells lacking receptors for the homing agent, by passive mechanisms; but rather it should only enter cells actively, by receptor-mediated endocytosis. The polymeric character of the drug construct should prevent its penetration of heart tissue, mitigating against a major shortcoming of daunomycin and other antitumor drugs.

On the other hand, the preferred molecular weight (MW) of the total conjugate is in the range of 10,000 to 100,000 D, and less than 50,000 D is especially preferred. The MW of the conjugate must be low enough so that it may penetrate solid tumors efficiently. It is known that Fab fragments of antibodies penetrate tumors better than the intact antibodies. [See Delabye, et al., (1986), J. Clin. Invest. 77: 301-11; Buchegger, et al. (1983), J. Exp. Med 158: 413-27; Buchegger et al. (1986), Cancer, 58, 655-61.] IgG antibodies have BWs of about 150,000 D prior to addition of any carrier molecules, and even Fab fragments, which are somewhat smaller, may be still be unable to penetrate tumors efficiently after conjugation with a carrier. By comparison, the prepared conjugates of the invention typically had a total MW of about 46,000 D, where the EGF is about 6,000 D and the polymer contributes most of the remaining 40,000 D. Free daunomycin has a MW of about 500 D, so several moles could be attached to each conjugate while maintaining the preferred MW range.

The aforementioned homing agent and polymeric moieties are conjugated either directly by peptide linkage, a secondary amide linkage of amino-acids, as in peptides and proteins, or, preferably, by a bridging unit of formula:

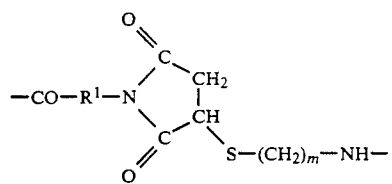

which m is 1 or 2 derives from a heterobifunctional reagent of formula:

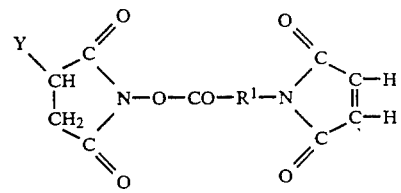

where $R^1$ is normally, but not restricted to: alkylene ($C_1$-$C_4$), preferably ($C_3$): phenylene, preferably (1,3-); cycloalkylene-alkylene preferably cyclohexylene-4-methylene; or alkylene-phenylene, preferably alkylene ($C_1$-$C_4$)-phenylene (1,4); and where Y=H or $SO_2ONa$, coupling being effected via an ethyl-mercaptan group linked to the terminal $H_2$—N group of the polymer moiety. Other heterobifunctional reagents differentiating reactive functions of the homing agent and polymeric moiety may also be employed.

In the most preferred embodiment, the therapeutic conjugate of the present invention is a conjugate of EGF with a polyglutamic acid carrier bearing one or more molecules of daunomycin. Such a conjugate should offer three fold specificity:
(a) specificity for tumor cells having high concentrations of EGF receptors, since these will more effectively bind and internalize the conjugate
(b) specificity for tumor cells having high levels of the enzyme γ-glutamyl transpeptidase since these will more readily degrade the PGA backbone and thereby liberate the daunomycin; and
(c) specificity for rapidly dividing tumor cells, since daunomycin is an antimitotic agent.

While it is of course desirable that the conjugate bind to all tumor cells and to no normal cells, it will be recognized that conjugates which bind only to certain tumor cells, and which bind to certain normal cells, may still show sufficient specificity for tumor cells to be of therapeutic activity.

Though in its preferred embodiment, the targeting agent of the conjugate also promotes internalization, it is conceivable that these functions could be performed by different moieties.

The text of the appended claims is hereby incorporated by reference into this specification as an enumeration of the preferred embodiments.

DETAILED DESCRIPTION OF THE INVENTION

Figure 1A:
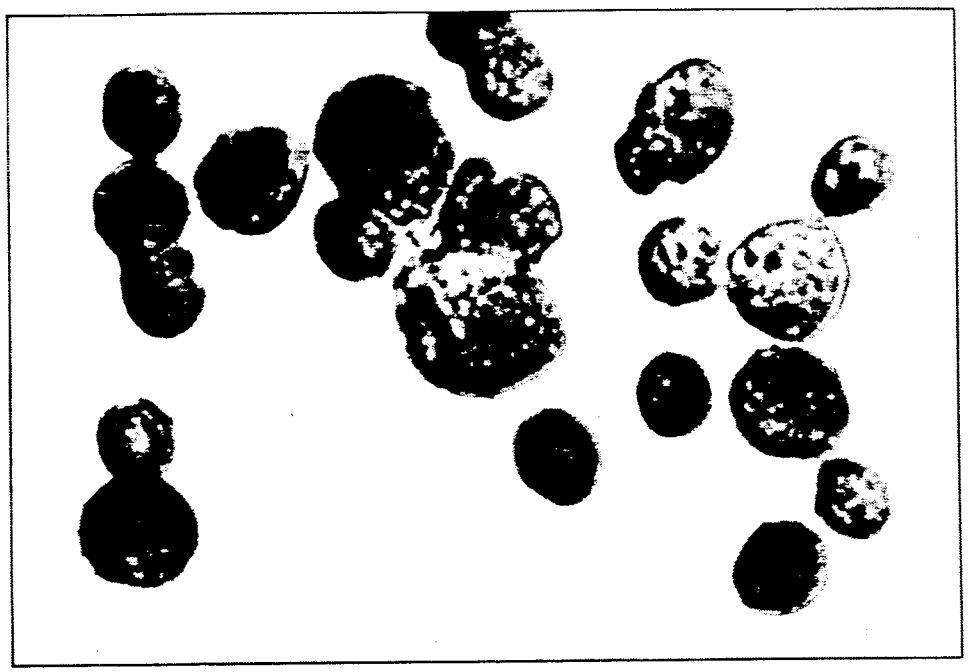
FIG. 1a is a photomicrograph of a culture of A431 human squamous carcinoma cell line used to test the effect of the compounds of the invention. The presence of large amounts of EGF receptors thereon is indicated by indirect immunoperoxidase staining (dark color).

The preferred new therapeutic compounds of the invention, using EGF or analogs as homing vector are of formula II:

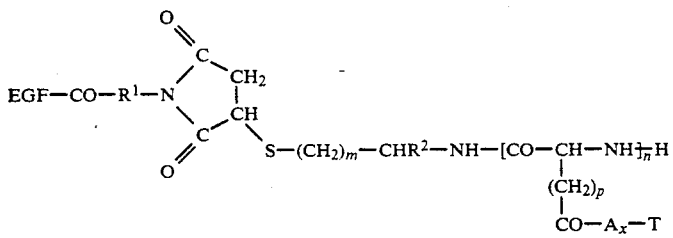

(II)

where m is 1 or 2, n is 20-300, p is 1 or 2, x is in the range 0-20, $R^1$ is alkylene ($C_1$-$C_4$), 1,3-phenylene, cyclohexylene-4-methylene, or alkylene $C_1$-$C_4$)-phenylene (1,4); and $R^2$ is H, or carboxyl, A is an amino-acid residue, or other bivalent moiety introduced to provide functionality for coupling of a cytotoxic substance, and T is hydroxyl or a cytotoxic substance. The monomer units of the polymeric moiety of formula III:

(III)

may vary in p, x, $A_x$, or T, with T being a cytoxic substance in at least one of the units.

EGF, a single polypeptide of 53 amino acids, can be extracted from submaxillary glands of mice [see J. Savage et al., (1972) J. Biol. Chem. 247, 7609] or it can be synthesized chemically, or by genetic engineering methods. for example using a cloned gene. EGF can also be of human origin.

The cytotoxic substance T and the $A_x$ moiety of formula II are normally covalently linked, the nature of the linkage dependent upon the functionality employed in the T and $A_x$ components. Primary amine functionality in the cytotoxic substance T (adriamycin, daunomycin, bleomycin, and melphalan) is normally employed in secondary amide linkage with a terminal carboxyl of $A_x$. Cytotoxic substances bearing the hydroxyl function (as in vinblastine and vincristine) are linked similarly as esters, or through carbonate linkage (A=an aminoalcohol residue, x=1), as exemplified by the linkage of norethindrone to poly (N-3-hydroxypropyl-glutamine) [see R. V. Petersen et al., (1979), Polymer Preprints, 20, 20]. Carboxylic acid functionality in the cytotoxic substance (as in methotrexate and chlorambucil) is brought into secondary amide linkage with side-chain amine functionality in $A_x$ (e.g., $A_x$ includes a diamino-acid residue), or into ester linkage (A=an amino-alcohol residue, x=1).

The cytotoxic substance T may also be a cytotoxic platinum complex analogous to cisplatin. The co-ordinate linkage of platinum compounds by the polymeric carrier may be achieved by the utilization as ligand of the γ-carboxy moiety of polyglutamic acid, or of amine or amino-acid or other ligand moieties incorporated in $A_x$; see Arnon, EP-A 190,464.

In formula II, $R^1$ is a group deriving from a heterobifunctional reagent employed in the elaboration of the linkage conjugating the preferred homing agent EGF and the polymeric moiety III. The conjugation is effected by the coupling of an N-substituted EGF derivative IV:

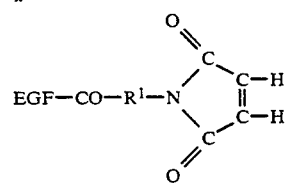

(IV)

and a derivative (V) of the polymeric moiety III:

HS—$(CH_2)_m$—$CHR^2$—NH—Moiety III    (V)

where m and $R^2$ are as defined previously.

The thiol-reactive compound IV is prepared by reaction of EGF with a heterobifunctional reagent VI:

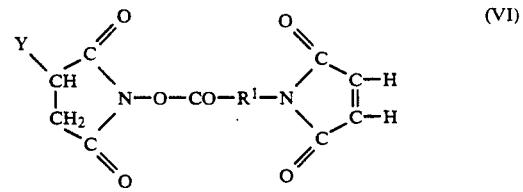

(VI)

where $R^1$ and Y are as previously defined. The utility of this, and other reagents (below), resides in the presence of both an acylating moiety, the N-hydroxysuccinimido ester moiety, and an alkylating moiety, the maleimido residue. Other reagents, conforming to this heterobifunctional character, which may be used for the generation of alkylating derivatives EGF, are m-maleimiobenzoyl-N-hydroxysuccinimide ester, m-maleimidobenzoylsulfosuccinimide ester, succinimidyl-4-(n-maleimidomethyl) cyclohexane-1-carboxylate, succinimidyl-4-(p-maleimidophenyl) butyrate, sulfosuccinimidyl-4-(N-maleimidomethyl) cyclohexane-1-carboxylate, sulfosuccinimidyl-4-(p-maleimidophenyl) butyrate. A good description of the use of these bridging agents can be found in the Pierce 1985-1986 Handbook & General catalog, page 326 onward. Other heterobifunctional reagents of the above character, or differentiating other functionalities in the components of the conjugate, could also be used.

The thiol-substituted polymer V is prepared following Kato et al., (1984), J. Med. Chem. 27, 1602-7. In brief, this involves the generation of a thiol-masked polymer derivative VII:

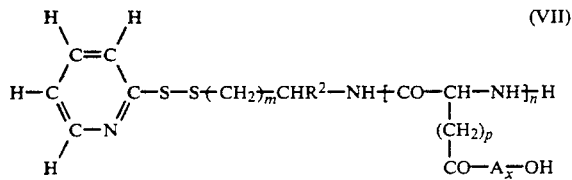
(VII)

where m, n, p, x, and $R^2$ are as previously defined, and partial substitution of the polymer side chains with the cytotoxic substance T, followed by removal of the 2-pyridylthio masking group.

In the preferred case, when T=daunomycin, the incorporation of the cytotoxic substance is achieved by a carbodiimide mediated acylation reaction. Two specific conjugates, which were prepared experimentally, can be illustrated by the following formulas:

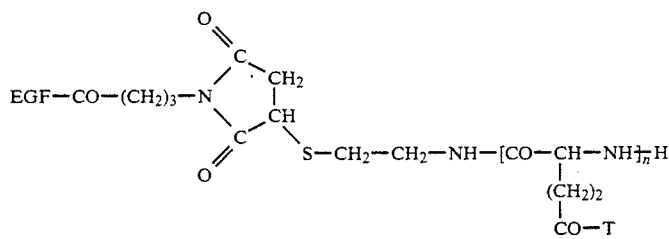
(VIII)

which is Formula II, where m is 1, n is 20-300, p is 2, x is 0, $R^1$ is $(CH_2)_3$, $R^2$ is H, and T is daunomycin or hydroxyl in a ratio of about 1 to 6;

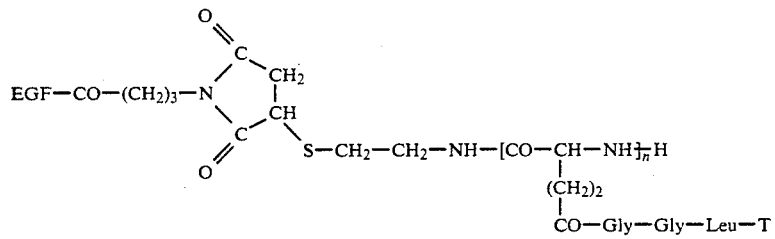
(IX)

which is Formula II, where m is 1, n is 20-300, p is 2, x is 3, $A_x$ is Gly-Gly-Leu, $R^1$ is $R^2$ is H, and T is daunomycin or hydroxyl in a ratio of about 1 to 6.

The introduction of the side-chain extension $A_x$, where A may vary among the common amino-acids, and x is preferably in the range 0-20, involves the usual techniques of peptide synthesis. [See, for examples, W.A.R. van Heeswijk, et al., (1985), J. Controlled Release 1, 301-315, and Hoes et al., (1985), J. Controlled Release 2, 205-213.]

Compound II demonstrates very useful properties in cancer therapy. In particular, Compound II is internalized by malignant cells and the cytotoxicity of the cytotoxic substance daunomycin is expressed therein. Its selectivity of action upon malignant cells is greater than that of known cytotoxic drugs. Thus, the first valuable property relates to its strong affinity toward malignant cells over normal cells.

Figure 1B:
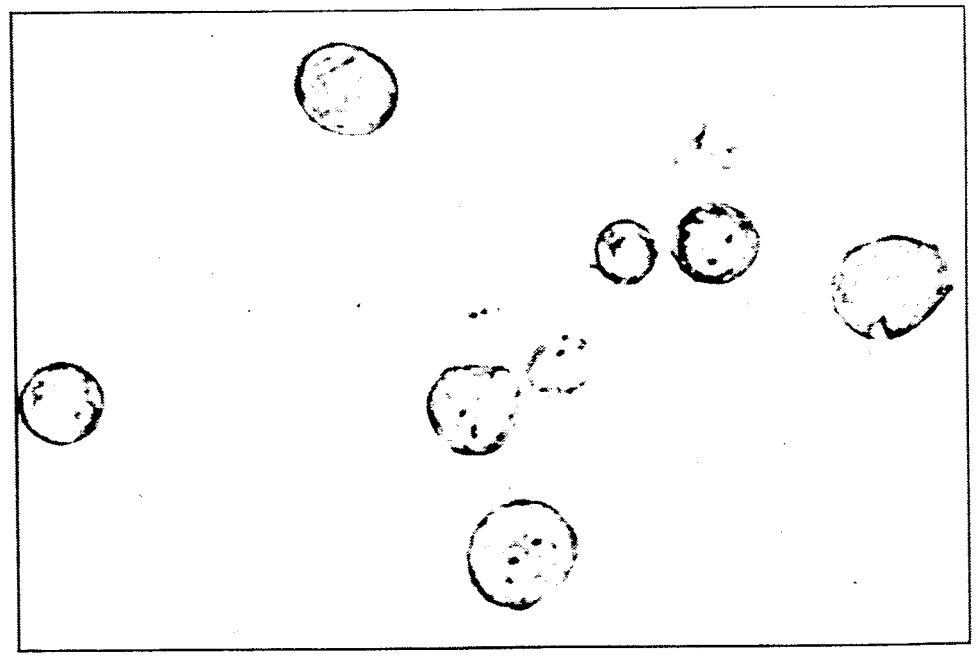
FIG. 1b is a photomicrograph similar to that of FIG. 1a, but of a culture of normal WI38 embryonic fibroblast cells used as a control. The low level of EGF receptors is indicated by the near absence of staining (light color).

For demonstrating this characteristic, a human squamous carcinoma cell line was selected, for instance A431 cell line shown in FIG. 1a [see M. D. Waterfield (1982), J. Cell. Biochem., 20, 149-161], although other tumor cells can be used as well. The membrane of these cells contains a very large concentration of EGF receptors which makes them highly suitable for tests with Compound II. The presence of these receptors is shown by indirect immunoperoxidase staining and appears as dark color areas of FIG. 1a. Control cell lines, for instance WI38 embryonic fibroblast cells with a low amount of EGF receptors (see FIG. 1b), were treated identically for comparison and appear as lighter color areas on the photomicrograph. It should be noted that the suitability of any given tumor for treatment with Compound II where EGF is the homing agent can be determined by means of measuring EGF receptors by tests such as the one described, for instance, in Example 2, below. Receptors for other homing moieties may also be detected by binding of appropriate antibodies or the homing substance itself.

When a known amount of Conjugate VIII (Compound II with p=2; x=0, T=daunomycin or OH in a ratio of 1 to 6) radio-labelled with $I^{125}$ (iodine is part of the EGF moiety) was incubated with A431 cells using WI38 cells as control, 31 percent of the total radioactive iodine was retained in the intra-cellular compartment and 2 percent in the membrane of the tumor cells, while in the control cells, the corresponding values were 2 percent and 0 percent, respectively. Using free EGF in place of Conjugate VIII in these experiments gave the corresponding 14 percent/0 percent and 7 percent/0 percent values instead. The reason for the greater accumulation of Conjugate VIII as compared to free EGF is possibly due to retention of EGF by the polymer backbone of Conjugate VIII by endocytic vesicles, whereas EGF is recycled freely back to the medium. Application of tests for internalization of a conjugate by appropriate receptor-bearing cells, such as that described in example 3, below, can be used to determined whether or not the homing substance in a given conjugate has retained its capacity for internalization, and, therefore, may be suitable for treatment of tumors.

A second valuable and unexpected property of Conjugate VIII relates to its enhanced toxicity as compared with free daunomycin toward malignant cells. This is illustrated by FIGS. 2a 2b.

Figure 2A:
FIG. 2a is a photomicrograph of an A431 cell line culture after a 48-hour incubation of 1 μg/ml of free daunomycin and testing for dead cells with Trypan Blue exclusion dye.
Figure 2B:
FIG. 2b is a photomicrograph similar to that of FIG. 2a, but after 48-hour incubation with, instead, 1 μg/ml of daunomycin in the form of conjugate VIII. The dark areas represent the killed cells.

In FIG. 2a, a culture of A431 cells is shown after 48 hrs incubation with a medium containing 1 $\mu$/g/ml of free daunomycin. Viability was scored by means of the Trypan Blue exclusion dye method. Exclusion of the dye from the cells demonstrates the viability thereof. In contrast, when an equivalent amount of daunomycin in the form of Conjugate VIII was used in a similar experiment (see FIG. 2b), a very large number of cells were killed as shown by the shrivelled up cells and the dark areas where the dye has accumulated.

Figure 3A:
FIG. 3a is a photomicrograph at time zero of a mixed culture of A431 and WI38 cell lines. The round cells are the tumor cells.
Figure 3B:
FIG. 3b is a photomicrograph similar to that of FIG. 3a showing the situation after 48-hour incubation with 1 μg/ml of conjugate VIII. The round tumor cells have greatly diminished.

The selectivity of Conjugate VIII toward tumor cells was further tested. For instance, FIGS. 3a and 3b show the effect of Conjugate VIII in the case of a mixed culture of A431 and WI38 cells. The round cells represent the A431 tumor cells and the elongated cells are the WI38 control cells. The culture medium was photographed at time zero (FIG. 3a). FIG. 3b illustrates this situation after 24 hrs in a medium containing 1 $\mu$g/ml of Conjugate VIII. It can be seen that the round darker malignant cells have strongly regressed. Testing similar to that described in examples 4, 5 and 7, below, can be performed to determine the enhancement of selectivity and/or potency of any given cytotoxin for any selected tumor cells provided by any desired form of Compound I.

In conclusion, it has been demonstrated that at equivalent molar concentrations (of daunomycin), Conjugate VIII was much more lethal to squamous carcinoma cells than free daunomycin itself. Also, Conjugate VIII has a selective mortal activity on tumor cells, but leaves normal cells alive, whereas under the same conditions, free daunomycin will kill normal cells.

The following examples illustrate the invention in more detail.

EXAMPLE 1

Synthesis of a Conjugate of EGF and Daunomycin-Grafted Polyglutamic Acid (Conjugate VIII)

Conjugate VIII was derived from a polymeric compound (VII) with a polyglutamate backbone structure (p 2, x=0), in which some $\gamma$-carboxylic groups are condensed with daunomycin and having a 2-pyridyl-dithio-ethylamido heading group (m=1, $R^2$=H), which was prepared according to Y. Kato, et al., 1984, J. Med. Chem., 27, 1602-1607 (compound 5 in scheme II of Kato).

The identity of the compound was checked analytically: MW=29,000 D by quantitatively determining the 2-pyridyldithio group; ratio of daunomycin to carboxylate 1/6 as determined by spectrometric quantitation of daunomycin at 480 nm.

To 25 mg of the polymer dissolved in 2 ml of 10 mM sodium phosphate buffer at pH 7 were added 0.1 ml of a 0.3 M solution of dithiothreitol (DTT). After 1 hr at 40° C., the solution was dialyzed overnight against a 0.1 M sodium phosphate buffer at pH 6.0 (SPECTRAPOR membrane, MW cutoff 3500); this regenerated the thio-ethylamido group of the molecule (compound 6 in scheme II of Kato); yield 23 mg of a red compound after freeze-drying (poly-(DM)-Glu-SH). The poly-(DM)-Glu-SH polymer was reacted with an excess of thiopropyl-SEPHAROSE in the pyridylsulfide form C; 12 hrs; phosphate buffer, pH 6) and the gel was rinsed with an excess of the same buffer in order to eliminate the polymer lacking the SH extremity. The polymer was conserved in this form in the cold. It was then regenerated by treating the gel with an excess of mercaptoethanol (12 hrs), dialyzed against water (overnight, 4° C.), and freeze-dried before reacting with EGF.

One hundred $\mu$g of EGF (SIGMA) was dissolved in 500 $\mu$l of 10 mM phosphate buffer, pH 7.0, containing 0.14 M NaCl. Then a quantity of $^{125}$I-EGF sufficient to provide an activity of 10,000 cpm/$\mu$g EGF was added followed by 50 $\mu$l of a 32 mM solution of N-succinimidyl-4-(N-maleimido)-butyrate (SMBU) (origin: Sigma), in dimethylformamide. The mixture was allowed to stand for 1 hr at 25° C., then it was dialyzed against a 0.1 M sodium phosphate buffer-0.1 M NaCl, pH 6.0, to eliminate the excess of SMBU.

The desired product (IV, $R^1$=$(CH_2)_3$) resulting from the condensation of SMBU and EGF was not isolated, but to the 500 $\mu$l of the dialyzed EGF solution were added 1 mg of poly-(DM)-Glu-SH and the mixture was slowly agitated overnight at 4° C. Five ml of thiopropylsepharose (pyridylsulfide form) were then added and the reaction was continued at 4° C. for 12 hrs. The gel was washed successively with 3 portions of 1 ml of sodium phosphate buffer, the eluent was concentrated under reduced pressure and subjected to gel filtration on SEPHADEX G75 (column 40×0.8 cm), using 0.1 M ammonium carbonate solution, pH 7.0. The fraction containing the EG-poly-(DM)-Glu conjugate (VIII), detected by absorption at 480 nm, was collected and freeze dried. Yield: 80 $\mu$g of solid.

EXAMPLE 2

Selection of A431 Test Cell Lines from Evidence of Receptor Concentration on the Cell Membrane by Indirect Immunoperoxidase Staining Indirect immunoperoxidase staining on cell lines were performed on trypsinized cells in 35 mm PVC plates. The surface was pre-treated with phosphate buffered saline (PBS) pH 7.2, the excess was then removed and the PBS washed cells ($10^5$/well in 50 $\mu$l PBS) were added to the plated and centrifuged for 5 minutes at 2000 rpm. 50 $\mu$l/well of 0.5 percent glutaraldehyde in cold PBS were then added to the dish and incubated for 15 minutes at room temperature. After two rounds of washes with PBS, the wells were filled with 100 mM glycine in a 0.1 percent BSA solution and allowed to stand for 30 minutes at room temperature to block glutaraldehyde activity. After two PBS washes, indirect immunoperoxidase was done by first denaturing the cells with an ice cold mixture of 99:1 ethanol-acetic acid for 30 minutes at 4° C. During this period, 3 $\mu$l of antibody were diluted in 1 ml PBS+1 percent fetal calf serum (FCS). The wells were than washed twice with PBS and incubated for 5 minutes with a solution of 20 percent FCS in PBS. This was then replaced by 200 $\mu$l/well of the antibody solution and incubated for 30 minutes at room temperature. The wells were then washed twice with PBS, once with PBS+0.1 percent Tween, and once again with PBS. 200 μl/well of a 1:400 dilution of swine anti-mouse peroxidase (POD) conjugated antibody (DAKO) in PBS 1 with percent FCS was then added for 30 minutes at room temperature. The wells were then washed twice with PBS, once with PBS+0.1 percent Tween and twice with distilled water. The in situ coloring was achieved by incubating the cells at room temperature with a solution of 10 ml 0.01 M phosphate buffer, pH 6.0, 5 μl, 35 percent oxygenated water and 100 μl of 1 percent ortho-dianisidin (MERCK) in methanol.

EXAMPLE 3

Internalization of Conjugate VIII in A431 Squamous Carcinoma Cells Compared to WI38 Fibroblasts The Conjugate VIII, radiolabeled with $^{125}I$ on the EGF, was incubated with confluent cell cultures of A431 and WI38 cells for 6 hrs at 37° C. in solution A (4 parts DMEM and 1 part of 50 mM Tris, 100 mM NaCl and 0.1 percent BSA adjusted to pH 7.4). The cells were then washed four times with ice-cold PBS+1 mM $CaCl_2$ and 1 mM $MgCl_2$. Fifty percent trichloroacetic acid was added in a proportion of 1:5 to the pooled solution A and PBS, and the mixture was counted on a gamma counter. The cell membrane was destablized by treatment on ice with 200 mM acetic acid and 150 mM NaCl (solution B) for 6 minutes. The solution B was then removed and the cells washed twice with solution B. These pooled B solutions were assayed for $^{125}I$. This treatment releases the EGF receptors bound to the cell surface. The cells were then completely dissolved in 0.2 N NaOH. The radioactivity found there represented the internalized Conjugate VIII. In control experiments, using free EGF $^{125}I$, a proportion of the EGF is recycled to the medium, therefore lowering the intracellular EGF. The results on the internalization of $^{125}I$ labelled EGF and Conjugate VIII in WI38 and A431 cell cultures are given in the following Table in terms of counts per min (background 30 cpm) for successively: EGF not integrated in the cell, EGF bound to the membrane, and EGF in the intra-cellular compartment. The percent of total cpm is given in brackets.

TABLE 1

| Internalization of free EGF and Conjugate VIII | | | |
|---|---|---|---|
| | | EGF cpm (%) | Conjugate VIII cpm (%) |
| WI38 | Unbound | 530 (93) | 1169 (98) |
| " | Membrane bound | 29 (0) | 28 (0) |
| " | Intracellular | 67 (7) | 52 (2) |
| A431 | Unbound | 536 (86) | 831 (67) |
| " | Membrane | 31 (0) | 57 (2) |
| " | Intracellular | 111 (14) | 390 (31) |

These results show that conjugate VIII is more efficiently internalized in malignant cells (31 percent) than in normal cells (2 percent).

EXAMPLE 4

Comparative Cytotoxic Effects of Free and Conjugated Daunomycin on A431 Squamous Carcinoma Cell All cells were maintained in Dulbecco's Modified Medium (DMEM), 10 percent foetal calf serum (FSC) (GIBCO), 2 percent penicillin-streptomycin (Gibco) and 1 percent fungizone (GIBCO) in 5 percent $CO_2$. They were plated at 50 to 60 percent confluence 24 hours before the addition of the toxin. 1 μg/ml of daunomycin, or equivalent in Conjugate VIII, was added in DMEM 10 percent FCS and the cell death rate visualized by trypan blue exclusion. Four volumes of 0.2 percent (w/v) Trypan Blue in water was freshly mixed with 1 volume of a saline solution 4.25 percent (w/v) of NaCl in water. One volume of this solution was mixed with 1 volume of PBS on the cell monolayer or to 1 volume of cell suspension in PBS. Observation and scoring took place 48 hours after addition of the toxin (see FIG. 2a and 2b). These results show that daunomycin is much more effective against malignant cells when in the form of Conjugate VIII than when in the free state.

EXAMPLE 5

Effect of Conjugate VIII on Mixed Cultures of Tumor (A431) and Normal (WI38) Cells)

Cells were maintained as described in Example 4. The WI38 fibroblasts were first plated and the A431 squamous carcinoma cells were plated the next day. The mixture culture was left growing for 24 hours and then 1 μg/ml of Conjugate VIII was added to DMEM 10 percent FCS. Nearly all the A431 cells were selectively killed after 24 to 48 hours whereas the WI38 fibroblast were left alive. Hence, the mixed culture became free from the tumor cells demonstrating that conjugate VIII can be used to separate the normal cells from cancer cells. The experiment was repeated but using only 0.1 μg/ml of Conjugate VIII (for the controls, equivalents of daunomycin were used in free form). Observation of the cultures after 15 days showed that the test samples contained no more of A431 cells, which situation was confirmed by continuing culturing for 6 weeks under normal conditions, this resulting in no reformation of tumor cells. In contrast, in the controls all cells, malignant and normal, had died after 15 days.

EXAMPLE 6

Synthesis of a Conjugate of EGF and Glycyl-Glycyl-Leucy-Daunomycin Grafted Polyglutamic Acid (Conjugate IX).

Conjugate IX was derived from a polymeric compound (VII) with a polyglutamate backbone structure (p=2, x=0) having a 2-pyridyldithio-ethylamido heading group (m=1, R2=H), which was prepared according to Y. Kato, et al., 1984, J. Med. Chem., 27, 1602–1607 (compound 5 in scheme II of Kato).

The polymer was subjected to the procedure reported by Hesswijk, et al., (1985), J. of Controlled Release 1 (4), 312, for extending the side chain with -Gly-Gly-Leu- ($A_x$ in formula II), as follows: 40 mg of the polymer and 68 mg of saccharin (0.31 mmole) were dissolved in 1 ml of DMF and the solution was allowed to stand for a few hours (solution A).

On the other hand, 0.32 mmole (40 μl) of N,N,'N'-tetramethylguanidine (TMG) were slowly added to a stirred suspension of 0.32 mmole (80 mg) of H-Gly-Gly-Leu-OH in DMF. Stirring was continued until all solids had dissolved (solution B).

Then, 0.43 mmole (70.3 mg) of N,N'-carbonyldiimidazole were added to solution A and, after stirring for 30 min, solution B was added. The mixture was further stirred for 3 days at room temperature. The mixture was added into 15 ml of 0.1 M phosphate buffer (pH 7.0) and the resulting solution was dialyzed into water (12 hrs), filtered on a Millipore membrane (0.45 μm) and the filtrate was freeze-dried. The polymer (yield 80 percent mg) was analyzed by hydrolyzing an aliquot in 6 N HCl for 12 hrs at 180 C. Determination of the amino acids in the hydrolyzate was carried out by High Performance Liquid Chromatography of the amino acid-phtalaldehyde derivatives (detection by fluorescence). The following ratio of glutamic acid:-glycine:leucine was measured: 0.95:2:1.

The pyridine-S group was removed with dithiothreitol according to Kato, et al., and analysis was performed by measuring the absorbance at 343 nm of the liberated pyridine-2-thione. Neglecting the presence of the TMG+ ion, a MW of 25,500 was found, meaning that in the product the degree of polymerization about 75-80.

The introduction of daunomycin was accomplished as follows: 33.7 mg (74.7 k μmole) of the side-chain extended polymer were dissolved in 15 ml of percent aqueous NaCl and 20 mg (35.5 mmole) of daunomycin hydrochloride were added. The pH was brought to 5.5 with 0.1 N NaOH after which 28 mg (0.1 mmole) of 1-ethyl-3-[3-(dimethylamino)]-carboiimide hydrochloride (EDC) were added under stirring.

After agitation for 18 hrs, the mixture was diluted with 15 ml of 1 M NaCl and dialyzed in water. The residue was freeze-dried which provided 31.6 mg of polymer. Splitting the disulfide with DTT as before and analyzing spectroscopically the pyridine-thione indicated the presence of about 10 DM per molecule, i.e. a ratio of labelled side-chains to unlabelled side-chains of about 1:7.

Conversion of an aliquot of the above disulfide to the desired thiol was done as follows: 2 mg of polymer were dissolved in 2 ml of 0.1 M phosphate buffer (pH 7.0) and 150 μl of 0.3 M DTT were added. After allowing to stand for 1 hr at 42 degrees, the solution was dialyzed for 24 hrs against freshly degassed phosphate buffer (pH 6.0); a SPECTRAPOR bag was used (MW cut-off=1000 D).

Simultaneously, EGF was activated by taking 0.2 mg of EGF (SIGMA) and dissolving in 0.75 ml of 10 mM phosphate buffer in 0.14 M NaCl, pH 7.0; then adding 0.5 ml of a 10 mg/ml SMBU solution in DMF. After 2 hrs at 20° C., the mixture was dialyzed at 4° C. against a 0.1 M Phosphate buffer containing 0.1 M NaCl at pH 6.0 (membrane MW cut-off=1000).

The overall volume of both the dialyzed polymer and dialyzed EGF solution were reduced to 1 ml by absorption with CMC powder, then they were mixed together and allowed to stand for 24 hrs in one dialysis bag. The mixture was chromatographed on SEPHADEX G75 (eluent 0.1 M NH$_4$CO$_3$) and the fractions absorbing at 480 nm were collected and cleaned from unreacted polymer by treating with thiopropylsepharose overnight at 4° C.. The gel was washed with 0.1 M NH$_4$CO$_3$ and 22.5 ml (O.D. of 0.176) of solution was collected. Yield was about 80 percent of conjugate IX. The respective weight contributions of DM and EGF in the product are about equal.

The presence and binding efficiency of the EGF factor in Conjugate IX was checked by immunoprecipitation with EGF antibody and attachment of the immunocomplex to a protein A-Sepharose gel (CL4B, Pharmacia). The procedure was as follows: Protein A-Sepharose gel was rehydrated to provide a 50 percent (V/V) solution in NET-NP40 buffer (100 nM NaCl, 1 mM EDTA, 1 mM EDTA, 10 mM Tris, pH 7.5, 0.5 percent NP40). Bovine serum albumin (BSA) was added to 120 μl of the buffered sepharose solution to provide a 0.3 percent (by weight) BSA solution (S).

On the other hand, BSA was added to 12 μl of a solution of antiserum against EGF (Collaborative Research) so as to provide a 0.3 percent by weight BSA solution in antiserum (Ab). Both (S) and (Ab) were incubated overnight at 4° C., then a quantity of Conjugate IX corresponding to 120 μg of daunomycin was added to sample Ab and incubated for 7 hrs at 4° C. under agitation. Then solution (S) was added and the mixture was agitated per 12 hrs at 4° C. A control (C) was prepared by adding the same quantity of Conjugate IX to another identical sample of solution (S). Both the above mixture (M) and the control were centrifuged for 5 min at 2000 rpm and the absorbance (A) of the supernatant liquid measured at 480 mm. The results are 0.41 for M and 0.955 for C, which shows that Conjugate IX contains EGF, the conformation of which is recognized by the antibody on the gel.

EXAMPLE 7

Toxicity of Conjugate IX and of Free Daunomycin Toward A431 Malignant and W138 (Control) Cells The toxicity of conjugate IX and of free daunomycin toward A431 malignant and W138 (control) cells was compared. The effect of these drugs was evaluated by the degree of inhibition of cellular protein synthesis. For this, we measured the level of incorporation of 35S methionine NEN) into newly synthesized proteins after a 48 hrs exposure to different concentrations of the drugs.

Cells were plated on 1.5 cm Petri dishes at 50 percent to 60 percent of confluence before the addition of the toxin. 0.1, 0.5 or 1 μg/ml doses of daunomycin (controls) or its equivalents in the form of Conjugate IX were added in DMEM 10 percent FCS. Cell death consecutive to this addition was measured as follows: the cells were exposed for 1 hour at 37° C. in 500 μl DMEM low methionine medium (GIBCO) containing radioactive $^{35}$S met. The medium was then removed and the dishes were washed with PBS 9137 mM NaCl, 2.7 mM KCl, 2.7 mM KCl, 8.1 mM Na$_2$HPO$_4$, 1.5 mM KH$_2$PO$_4$, 0.9 mM CaCl$_2$, 0.5 mM MgCl$_2$, pH 7.2). These solutions were stored for beta counting. The cells were lysed with 1 ml 0.1 N NaOH and placed in a tube with 500 μl Trichloroacetic acid (TCA) 10 percent to precipitate the proteins. This mixture was filtered on GF/A filters (Whatman) to eliminate unreacted $^{35}$S-met. The filters were washed twice with 1 ml of 10 percent TCA and once with 100 percent ethanol. The filters were dried at 80° C. for 2 hours and subjected to beta counting in Econofluor (NEN) scintillation medium. The results reported in the following table 2 Show that Conjugate IX is very cytospecific but less cytotoxic than daunomycin alone.

TABLE 2

| Toxicity of Conjugate IX and of Free Daunomycin | | | |
|---|---|---|---|
| | Drug Concentration (μg/ml) | % of protein Synthesis A431 | Inhibition WI38 |
| Free Daunomycin | 0.1 | 30 | 10 |
| | 0.5 | 68 | 46 |
| | 1.0 | 97 | 80 |
| Conjugate IX | 0.1 | 4 | 0 |
| | 0.5 | 17 | 6 |
| | 1.0 | 47 | 4 |

EXAMPLE 8

In Vivo Test of Conjugate VIII

Tumors were induced by injection of $5 \times 10^6$ A431 cells into nude mice, and when the tumors reached 3 to 5 mm, 0.1 mg/kg of daunomycin, either in the form of conjugate VIII (see example 1) or in free form was injected into two sets of nude mice. In the prior art, up to 10 mg/kg doses have been used in mice (S. Schwarz, et al., 1975, Cancer Chem. Rep., 6, 2, 107-114). The drug was injected either directly in the tumor or in the caudal vein 4 times at 3 days intervals. The measures were taken a week after the last injection.

By visual inspection of the animals, it was noted that the growth of the tumors treated with conjugate VIII was significantly reduced, as compared to control mice or to treatments with free daunomycin. These results were similar whether the injection of the drug was directly in the tumor or in the caudal vein which shows that biodegradation and release of the cytotoxic substance occurs substantially only in the target cells. Results are shown in the following table 3.

TABLE 3

| | In Vivo Test of Conjugate VIII | | |
|---|---|---|---|
| Injection | Initial Surface of the Tumor (A) | Final Surface of the tumor (B) | Growth coefficient (B/A) |
| Daunomycin I.V.* | 30.5 | 500 | 16.4 |
| Conjugate VIII I.V. | 25 | 54 | 2.2 |
| Daunomycin I.T.** | 9 | 170 | 18.7 |
| Conjugate VIII I.T. | 9 | 50 | 5.6 |
| Control*** | 9 | 320 | 35.6 |

*I.V. = intra-venous
**I.T. = intra-tumor
***Placebo injection

At the end of the experiment, the tumors were dissected and weighed. Results are given below. If corrections for slight differences of tumor size at the beginning of the treatment are taken into account, it can be seen that the results (Table 4) correlate well with the surface estimate given in the previous Table 3.

TABLE 4

| In Vivo Test of Conjugate VIII (Tumor Weights) | | |
|---|---|---|
| Daunomycin | I.T. | 1.178 g |
| Conjugate VIII | I.T. | 0.359 g |
| Daunomycin | I.V. | 6.789 g |
| Conjugate VIII | I.V. | 0.816 g |

In conclusion, the compounds of the invention show better performances in selectively killing squamous carcinoma cells than daunomycin, both in vitro and in vivo. In the animal tests, we noted that very low amounts of conjugate VIII have a remarkable effect on tumor growth.

EXAMPLE 9

In Vivo Test of Conjugate IX

The in vivo tests reported in Example 8 were repeated using Conjugate IX. Thus, 2 mg/kg of daunomycin, free or in the form of Conjugate IX were injected every 3 days over 9 days in the caudal vein of nude mice bearing A431 tumors. The tumor growth inhibition by conjugate IX was significantly greater than by free daunomycin (D), free EGF or DM labelled but untargeted polymer (DMA). These results are shown in the Table 5 below where the values correspond to tumor diameter (in mm) measured with a calliper after a number of days. The lethal dose of Conjugate VIII and Conjugate IX have not been measured but are presumably less toxic than free daunomycin which enters freely into most normal cells.

TABLE 5

| | In Vivo Test of Conjugate IX | | | | |
|---|---|---|---|---|---|
| Days: | 0 | 4 | 7 | 11 | 14 |
| Control | 10 | 14 | 17 | 22 | 24 |
| Daunomycin | 10 | 12 | 15 | 20 | 21 |
| Free EGF | 10 | 13 | 14 | 17 | 17 |
| Polyglu-DM | 10 | 11 | 12 | 16 | 17 |
| Conjugate IX | 10 | 11 | 12 | 14 | 15 |

We claim:

1. A therapeutic chemical conjugate including EGF as a first moiety, and a second moiety linked covalently to the EGF, said second moiety comprising a plurality of repeating units, each unit having the structure

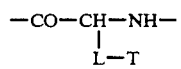

where L is selected from the group consisting of polyglutamic acid and polyaspartic acid, and T is selected from the group consisting of anthracycline drugs, bleomycin, melphalan, chlorambucil, cisplatin, adriamycin, daunomycin, and daunorubicin, and where said conjugate has a molecular weight of between 10,000 and 100,000 D and is effective in target cells in vivo and is internalized by tumor cells whereby the latter are inhibited or destroyed.

2. The conjugate of claim 1 wherein L is polyglutamic acid and T is daunomycin.

3. The conjugate of claim 1, where the EGF is essentially identical to human EGF.

4. The conjugate of claim 1, wherein the first moiety is directly linked to the second moiety by means of a peptidyl linkage.

5. The conjugate of claim 1 wherein the first moiety is linked to the second moiety by a structure having the formula:

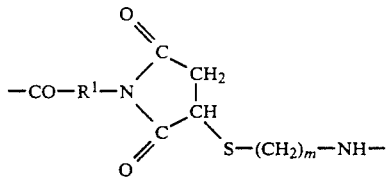

where R' is: alkylene ($C_1$-$C_4$); 1,3-phenylene; cyclohexylene-4-methylene; or alkylene ($C_1$-$C_4$)-phenylene (1,4); and m=1 or 2.

6. The conjugate of claim 1, having a molecular weight of less than about 100,000 D.

7. The conjugate of claim 1 wherein the T is selected from the group consisting of anthracycline drugs, bleomycin, melphalan, chlorambucil, and cisplatin.

8. The conjugate of claim 7 wherein the T is selected from the group consisting of adriamycin, daunomycin, and daunorubicin.

9. The conjugate of claim 1 wherein the T is daunomycin.

10. A therapeutic composition comprising the chemical conjugate of claim 1 and a therapeutically acceptable carrier having a molecular weight of between 10,000 and 100,000 D.

* * * * *